United States Patent
Baccanti

[11] Patent Number: 5,429,946
[45] Date of Patent: Jul. 4, 1995

[54] PROCESS AND APPARATUS FOR ELEMENTAL ANALYSIS OF HALOGENS

[75] Inventor: Marco Baccanti, Milan, Italy
[73] Assignee: Fisons Instruments S.p.A., Italy
[21] Appl. No.: 974,558
[22] Filed: Nov. 12, 1992
[30] Foreign Application Priority Data
Nov. 12, 1991 [IT] Italy .................. MI91A3012
[51] Int. Cl.⁶ .................................... G01N 33/00
[52] U.S. Cl. ...................... 436/103; 422/78; 422/80; 422/88; 422/98; 436/119; 436/124; 436/160
[58] Field of Search .......... 422/78, 80, 81, 82, 422/58, 78, 88, 89, 98; 436/124, 125, 119, 123, 103, 160

[56] References Cited
U.S. PATENT DOCUMENTS

| | | | |
|---|---|---|---|
| 2,136,741 | 11/1938 | Henne | 436/124 |
| 3,428,432 | 2/1969 | Staunton et al. | |
| 3,716,334 | 2/1973 | Pont | 436/124 |
| 3,819,499 | 6/1974 | Hoogeveen et al. | 204/195 S |
| 3,985,505 | 10/1976 | Bredewig | 436/160 |
| 3,992,151 | 11/1976 | Vanderhoeden | 436/124 |
| 4,054,414 | 10/1977 | Grob et al. | |
| 4,160,802 | 7/1979 | White et al. | 422/78 |
| 4,198,208 | 4/1980 | Lerner et al. | 422/78 |
| 4,234,315 | 11/1980 | Scott | |
| 4,401,763 | 8/1983 | Itoh | 436/115 |
| 4,407,963 | 10/1983 | Sorensen | 422/58 |
| 4,467,038 | 8/1984 | Scott | 422/89 |
| 5,073,502 | 12/1991 | Steele | 436/125 |

FOREIGN PATENT DOCUMENTS

| | | | |
|---|---|---|---|
| 0544142 | 6/1993 | European Pat. Off. | |
| 1567291 | 5/1969 | France | |
| 901767 | 3/1991 | Germany | |
| 77588 | 7/1978 | Japan | 436/124 |
| 1172262 | 2/1967 | United Kingdom | 436/124 |
| 965992 | 10/1982 | U.S.S.R. | 436/124 |
| 1321222 | 3/1988 | U.S.S.R. | 436/124 |

Primary Examiner—Robert J. Warden
Assistant Examiner—Krisanne M. Thornton
Attorney, Agent, or Firm—Lerner, David, Littenberg, Krumholz & Mentlik

[57] ABSTRACT

The determination of the halogen content in a substance is carried out by oxidative combustion of the sample under a continuous flow of gas, in the presence of oxygen, the gases coming out of the combustion reactor being then carried by gas flow to analysis equipment.

21 Claims, 2 Drawing Sheets

PROCESS AND APPARATUS FOR ELEMENTAL ANALYSIS OF HALOGENS

FIELD OF THE INVENTION

The present invention relates to a process and an apparatus for elemental analysis of halogens. The process and method are also suitable for determining the content of other elements, such as S and P, contained in the same substance.

BACKGROUND OF THE INVENTION

The known technique currently used for elemental analysis of halogens envisages to oxidize by combustion a known amount of the sample inside a flask containing oxygen at a predetermined pressure. The combustion gases are then absorbed by manually stirring on an aqueous solution provided within the oxidation flask. The obtained solution is then titrated in a known way in order to determine the quantity of halogens present in the substance. Should individual determination of halogens be required, the solution may be submitted to separation and detection of the separated compounds.

It is evident that this method, totally manual, is extremely slow and time consuming, especially if compared to elemental analysis techniques for C, H, N, S, that are almost completely automated.

OBJECTS OF THE INVENTION

It is the aim of the present invention to solve the aforementioned problems by means of a process and an apparatus enabling the automation of halogens analysis, reducing the analysis time, while ensuring high accuracy, reliability and reproducibility of results.

SUMMARY OF THE INVENTION

This aim is achieved by means of the present invention, that relates to a process for elemental analysis of at least the halogen content in a sample by means of combustion of a known quantity of said sample and analysis of the resulting oxidation gases, characterized in comprising the following steps:

feeding a continuous flow of gas to a heated oxidation reactor; feeding said sample to said heated reactor; carrying out a flash combustion of said sample in the presence of oxygen; and carrying the combustion gases thus obtained to analysis equipment by means of said continuous gas flow.

The invention also relates to an apparatus for elemental analysis of at least the halogen content of a sample by means of combustion oxidation of said sample in a heated reactor, characterised in that it comprises:

means for feeding a continuous flow of gas to said combustion reactor; means for feeding oxygen gas to said reactor; and means for collecting combustion gases coming from said combustion reactor and conveying them to analytical means.

According to the invention, the weighed sample of the substance to be analyzed is fed to the combustion reactor in a very short time, so as to oxidation of the substance (flash combustion).

According to preferred feature of the invention, the combustion gases coming from the reactor are collected and absorbed in an aqueous solution of hydrogen peroxide that is eventually titrated in a known way, for instance by electrochemical methods. In a preferred embodiment gas flow and aqueous solution are sent together as continuous flows to an absorption vessel provided with interface means to facilitate absorption of combustion gases in said solution.

According to required analysis, the combustion gases absorbed in hydrogen peroxide solution may be detected directly or after preliminary separation into individual components (e.g. by ion chromatography).

The advantages in time saving and easier performance achievable by means of the present invention are evident, particularly when considering that it is possible to carry out the automatic sampling of the substance and then the combustion-oxidation and the analysis in succession of a plurality of samples.

The invention will be now further described with reference to the accompanying drawings given with illustrative and non limiting purposes, where:

DESCRIPTION OF THE PREFERRED EMBODIMENTS

Figure 1:
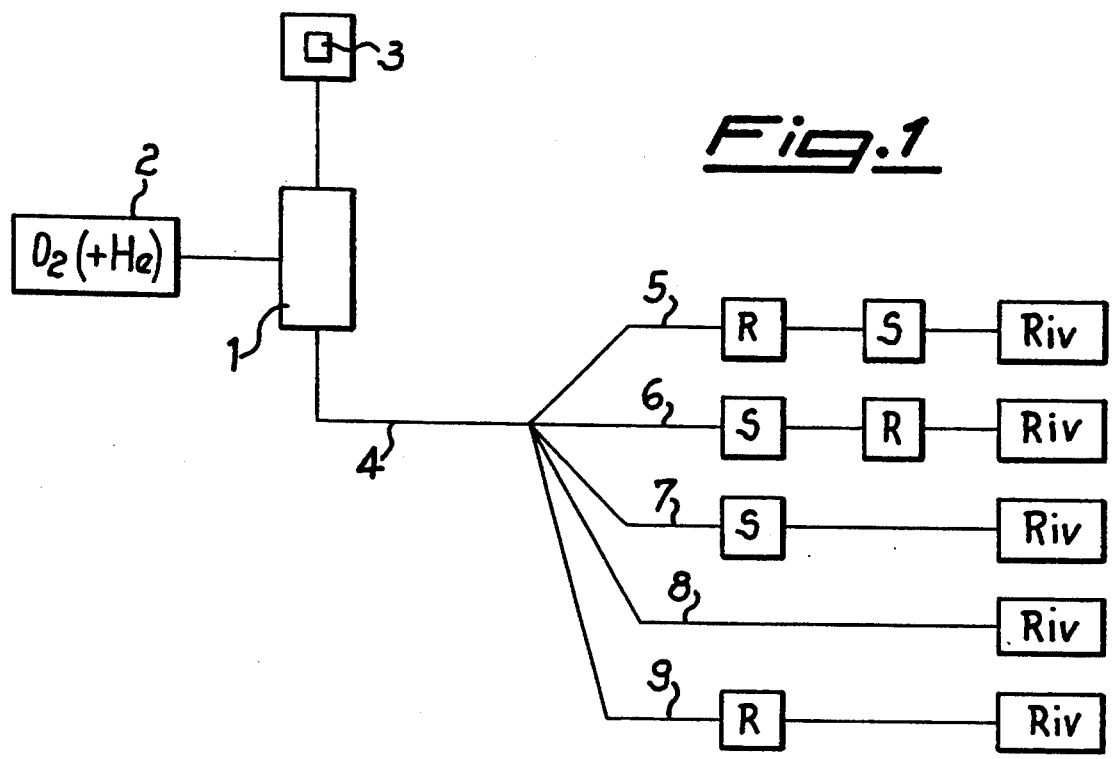
FIG. 1 is a block diagram of the possible stages of an apparatus according to the invention.

Referring first to FIG. 1, the process according to the invention envisages to feed a continuous flow of gas from gas source 2 to combustion-oxidation reactor 1, previously brought to the temperature of combustion of the sample, usually of about 1000 degrees C.

A sample 3 of known weight, up to 15 mg, of the substance to be analyzed, is then fed into reactor 1 and oxidized by flash combustion in the presence of oxygen.

Figure 3:
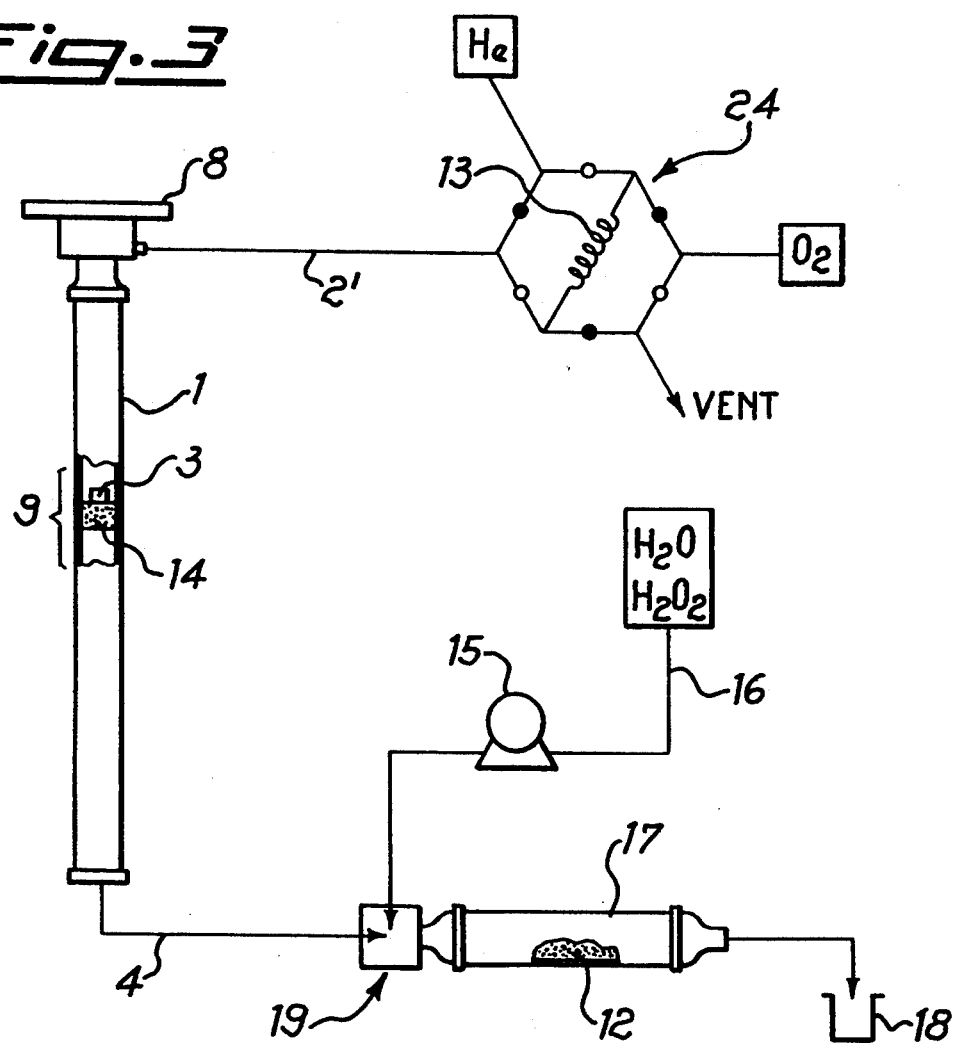
FIG. 3 is a schematic view of a further embodiment of the invention.

The oxygen may be fed as a constant gas flow, i.e. the oxygen acts also as carrier gas; alternatively, an amount of oxygen sufficient to carry out sample oxidation is first stored in metering and storing means such as loop 13 in FIG. 3, and is thereafter fed to reactor 1 when the sample is fed, in order to carry out the required flash combustion. In the latter case, the carrier gas is an inert gas and preferably is Helium.

The sample combustion gases thus obtained are then carried by the gas flow out of reactor 1 into duct 4, then drawn (references 5 to 9).

If the sample is in a particulate, liquid or powder form, it is usually placed inside a capsule made of tin (Sn) or similar metal oxidizing with strongly exothermic reaction. In other cases, e.g. in analysis of plastic materials, the sample per se may be fed to the reactor.

Figure 2:
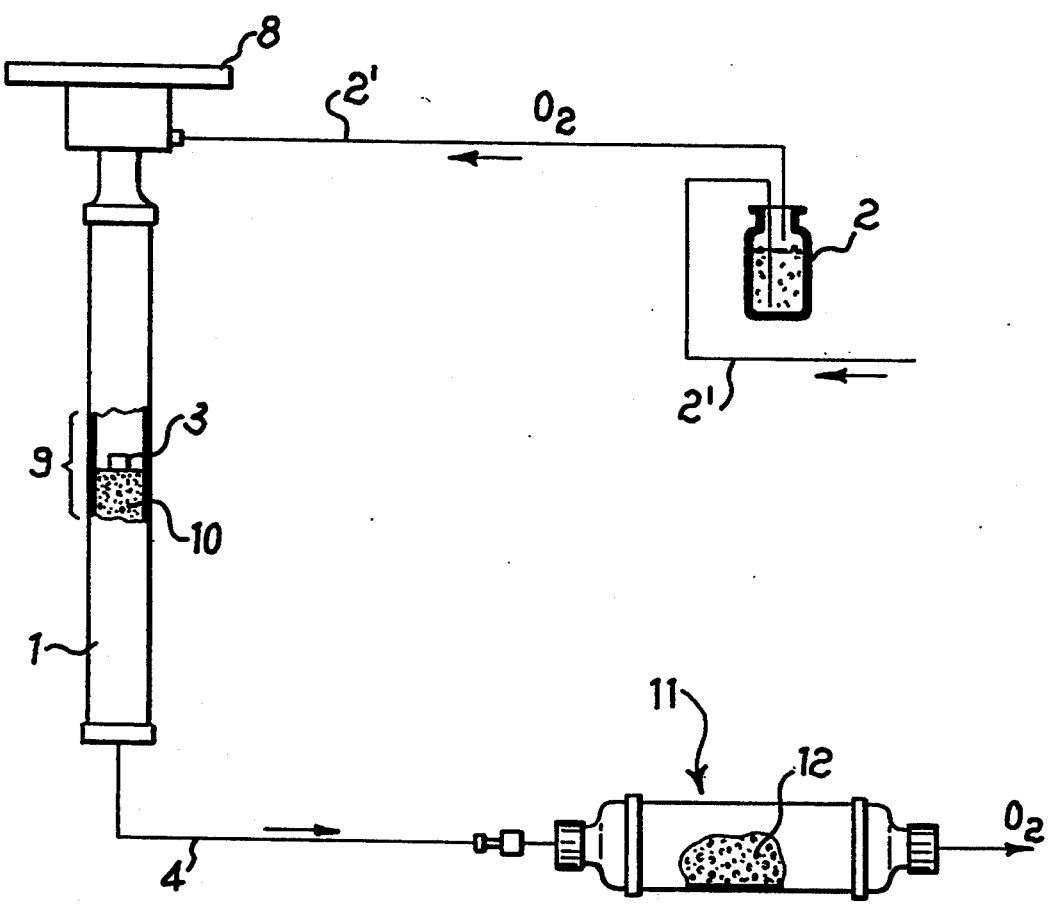
FIG. 2 is a schematic view of an apparatus according to the invention.

Reactor 1 is, as disclosed in FIGS. 2 and 3, of the vertical type similar to that known in the art for performing elemental analysis of C, H, N. It is thus possible to fed the samples by dropping them into reactor 1, and to feed in succession many samples, for instance by means of an automatic sampler, avoiding to remove each time the sample container from the reactor and subsequently restore therein the required atmosphere. The sample is fed into the reactor in a very short time directly into the hotter portion of the reactor where a flash oxidation-combustion of the substance takes place, also thanks to the heat generated by the capsule oxidation, if any, heat that temporarily increases the temperature inside the reactor, in the area where the sample is, from 1000 degrees C. to 1700–1800 degrees C.

As previously mentioned, combustion gases generated from flash combustion are carried by the continuous flow of gas (either oxygen or helium) to their analysis equipments. For this analysis step different methods can be used, according to the type of analysis that is carried out. FIG. 1 illustrates five different possibilities of treatment of combustion gases.

According to a first path (5), gases are first collected in R then separated in S and finally conveyed to ion detection in Riv. Alternatively (6), first of all gases are separated (S) and individual collection of separated compounds including halogens is carried out (R), to eventually detect (Riv) the single compounds, for instance by means of electrochemical detectors.

Another alternative (7) consists in separating gases (S) and performing their detection (Riv) without collection (e.g. by means of gas chromatographic detectors or mass spectrometers). It is also possible to detect the products of combustion without any previous separation. Said detection (Riv) can take place directly in gaseous phase (8) or after collection (R) of gases in liquid phase (9). FIG. 2 discloses an apparatus according to the invention to perform elemental analysis of halogens and other possible ions by following above mentioned path "Collection Separation - Detection" indicated by 5 in FIG. 1.

In this case collection step is implemented by sending the combustion gases as carried by the continuous gas flow, through an aqueous solution of hydrogen peroxide where the combustion products are absorbed and retained as ions. It is a further advantage of this analysis mode the possibility of detecting, besides Cl, Br, and I ions, also P and S as phosphate and sulfate ions, respectively.

The apparatus is comprising reactor 1, generally made of quartz, heated at its central portion at a temperature of approximately 1000 degrees C., and a line 2' for feeding a continuous flow of oxygen to reactor 1. In FIG. 2 is disclosed a bubbler 2 containing distilled water, wherein oxygen is passed to be humidified. However, this is not necessary and is useful only in some cases.

A line 4 is connecting reactor 1 with absorption vessel 11, where combustion gases are collected by absorption on an aqueous solution of hydrogen peroxide.

On top of reactor 1, which is positioned vertically, there is provided sampling means 8 for feeding sample 3, such as for instance an automatic sampler of known type and used in the instruments for C, H, N, S elemental analysis. In reactor 1 are provided quartz wool layer 10 serving as support to sample 3 and/or sample ashes in correspondence to central portion 9 of reactor 1, i.e. the reactor area that is heated at the highest temperature. Supporting means 10 should be selected and dimensioned in order to enable an easy flow of oxygen around sample 3 while it undergoes flash combustion. The duct 4 coming out of the reactor 1 is made of inert material such as peek, TEFLON or the like and is connected in a known way to above mentioned collecting vessel 11.

Said vessel is consisting of a container inside which there is provided a plurality of interface means 12 such as quartz shavings 12, glass or quartz wool or any means wetted with an aqueous solution of hydrogen peroxide and suitable to provide a high gas-liquid interface area for combustion products absorption. Other suitable means for having a high gas-liquid interface area is a vessel 11 having a plurality of wall portions projecting within the vessel as in a VIGREUX equipment.

Independently of the interface means used in the absorption vessel, it was found that this kind of trap is suitable for quantitatively retaining $Cl_2$, $Br_2$, $I_2$ or their halide acids present in the products of oxidation, letting only the oxygen flow escape. These products are reacted with hydrogen peroxide in the aqueous solution to quantitatively yield respective halide ions in said aqueous solution, where they are retained. Moreover, as previously mentioned, also S and P are retained as sulfates and phosphates.

To carry out the analysis, after the gases have been absorbed in vessel 11, the latter is washed with distilled water and the percolate is collected. For halogen, P and S determination, the simplest way is the one that foresees to collect the percolate in a flask, then to bring the flask content to known volume and to separate different ions, for example by means of ion chromatography. The compounds thus separated are finally titrated in a known way, e.g. by methods of electrochemical detection.

The system can be completely automated, for instance as disclosed in FIG. 3.

According to this embodiment, the solution of hydrogen peroxide is fed as a continuous flow to absorption vessel 17 and collecting means are comprising also pump means, most preferably a peristaltic pump 15, connected by line 16 to a reservoir for aqueous solution of hydrogen peroxide, and to T piece 19, to which also line 4 is connected.

Figure 4:
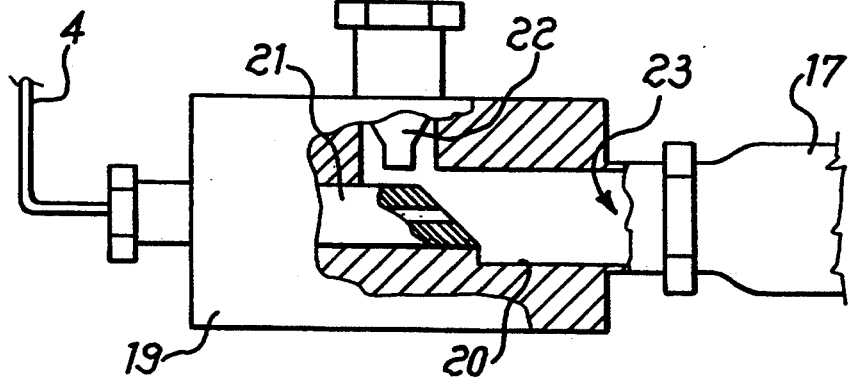
FIG. 4 is a schematic, partially sectional view of a connector piece to be used in the invention.

In FIG. 4 is shown a T-piece suitable for use in present invention. In this embodiment first element 21, connected to line 4, is longer than element 22, connected to line 16. The output exit of element 21 is thus nearer to port 23 than exit of element 22.

The two flows reaching T piece 19 and going through vessel 17 with interface means 12 perform the absorption of combustion products in the aqueous solution of hydrogen peroxide. For the scope of present invention, the flow obtainable from peristaltic pump 15 is considered a continuous flow.

The outcoming liquid solution is then collected in a tray for fractions either through a washing with distilled water, or by simply continuing the solution flow through vessel 17 also between two subsequent analysis. Alternatively all the aqueous solution corresponding to the combustion of a sample may be collected in a vessel 18. The thus collected solution is thereafter analysed in any known way.

An advantage of FIG. 3 embodiment is that vessel 17 is self-purging, in fact to this purpose it is sufficient to continue the solution flow through vessel 17 after all the solution containing the compounds of interest has been collected.

A further difference of FIG. 3 embodiment from that of FIG. 2 is the oxygen feeding mode. According to this mode, the continuous flow of gas is a flow of inert gas, preferably of helium. Oxygen required for combustion is first stored in a loop 13 having known volume in order to meter the oxygen while storing it. When it is required, i.e. when sample 3 is fed to reactor 1, the stored oxygen is fed through line 2' to reactor 1 to carry out a flash combustion.

Commuting from Helium flow to He+$O_2$ flow and then back to the flow is obtained by means of suitable valve means such as the 6-port valve 24 schematically shown in FIG. 3. A valve of this kind is known in the art.

It should however be clear that line 2' of FIG. 3 may also be connected to a source of oxygen only, i.e. that FIG. 3 embodiment can work with a continuous flow of $O_2$, as in FIG. 1, preferably without bubbler 2.

In reactor 1 the preferred supporting means for sample and/or sample ashes is quartz wool 14, or similar means such as a bed of quartz shavings in a limited amount. Actually it was found that, as previously discussed with reference to FIG. 2, optimum oxidations are obtained if there is as little volume of supporting means as possible and if there is an empty space at the lower end of reactor 1. Moreover, reactor 1 internal diameter at central portion 9 should not be much greater than sample diameter to obtain optimum oxidation.

Preferred analysis condition according to FIG. 3 embodiment are as follows:

He flow 20–200 ml/min; $O_2$ 5–50 ml at 150–250 KPa; sample 0.1–10 mg; hydrogen peroxide solution concentration (v/v) from 3% to 10 ppm; hydrogen peroxide solution flow 1–20 ml/min; aqueous solution collected volume 0.5–15 ml; purge time between two analysis 1–2 min; peek or TEFLON lines internal diameter 0.05–1.0 mm.

The invention will now be further disclosed by means of the following example.

Example

A sample of commercial polypropylene plastic material was analysed in an apparatus according to the present invention and having the following features and analysis conditions:

reactor length 45 cm; reactor internal diameter 12 mm; supporting means for sample and ashes in reactor central portion: 3 cm quartz wool;
connecting tubing (4) in Peek with internal diameter of 0.1 mm and 10 cm length;
absorption vessel 10 cm long and with internal diameter of 0.8 cm;
aqueous solution of 0.1% (v/v) hydrogen peroxide;
aqueous solution flow 8 ml/min;
continuous gas flow of oxygen without helium, 30 ml/min;
collected fraction of eluted sample from absorption vessel 5 ml;
purge time between two subsequent analysis 2 minutes;
sample weigth about 3.2 mg.

After 10 analysis and relevant measurements the following average values and standard deviation (in ppm w/w) were obtained:
Cl theoret.=1280
Cl found=1240
Std dev.=24
P theoret.=230
P found=260
Std dev.=37
S theoret.=1600
S found=1540
Std dev.=50

As already mentioned, other methods for the treatment of the gases of combustion-oxidation are equally acceptable; for example, gases can be submitted to gas chromatography isolating the halogen-containing fractions and titrating such fractions, using different types of gas chromatographic detectors (heat conductivity detectors, conductometric detectors, mass spectrometers, and so on). It is also possible to perform the direct detection of halogens by the use of specific methods, such as mass spectrometry of combustion gases. In this case, line 4 will be connected to mass spectrometer by means of a suitable interface comprising a splitting valve and an auxiliary pump. A mass spectrometry equipment suitable for this purpose is e.g. QTMD 100 or QTMD 150 manufactured by the applicant. It should be noted that by this means of analysis, besides elements above cited, i.e. Cl, Br, I, P, S, also Nitrogen can be quantitatively detected.

I claim:

1. A process for elemental analysis of at least one of the halogen, phosphorous or sulfur content in a sample comprising the steps of:
   feeding a continuous flow of gas into a heated flash combustion reactor; feeding a halogen, phosphorous or sulfur-containing sample into said flash combustion reactor; maintaining said flash combustion reactor at a temperature sufficient to cause the flash combustion of said sample while feeding said sample into said flash combustion reactor; oxidizing said sample by flash combusting said sample in the presence of oxygen in said flash combustion reactor; and continuously carrying the combustion gases obtained by said flash combustion of said sample to analysis equipment by means of said continuous flow gas.

2. The process according to claim 1, said continuous flow of gas comprises a continuous flow of inert carrier gas and said oxygen gas required for flash combustion is fed from storing means to said flash combustion reactor when said sample is fed to said flash combustion reactor.

3. The process according to claim 1, wherein said continuous flow of gas comprising a continuous flow of oxygen gas acting as a carrier gas.

4. The process according to claim 1, wherein said combustion gases are fed to absorption means containing an aqueous solution of hydrogen peroxide and are contacted with said solution to absorb therein combustion products contained in said combustion gases.

5. The process according to claim 4, wherein said solution of absorbed gases is analyzed by electrochemical methods.

6. The process according to claim 4, wherein said solution of absorbed gases is subjected to ion chromatography, prior to being analyzed.

7. The process according to claim 1, wherein said combustion gases are analyzed in a gaseous state.

8. The process according to claims 4, 5 or 6, wherein said aqueous solution of hydrogen peroxide is fed as a continuous flow to said absorption means.

9. An apparatus for elemental analysis of at least one of the halogen, phospohrous or sulfur content of a sample comprising:
   a flash combustion reactor capable of being maintained at a flash combustion temperature during the feeding of a sample;
   feeding means for feeding a continuous flow of gas to said flash combustion reactor;
   sample feeding means for the sequential feeding of a halogen, phosphorous or sulfur containing sample into said flash combustion reactor and effecting the oxidation of said sample by flash combustion in the presence of oxygen gas in said flash combustion reactor;
   and collecting means for collecting combustion gases coming from said flash combustion reactor and conveying them to analytical means connected thereto.

10. The apparatus according to claim 9, wherein said collecting means comprises at least one absorption vessel provided with an aqueous solution of hydrogen peroxide to absorb therein combustion products contained in said combustion gases.

11. The apparatus according to claim 9, wherein said feeding means comprises carrier gas feeding means for continuously feeding inert carrier gas to said flash combustion reactor, and storing means for intermittently dispensing said oxygen gas to said flash combustion reactor, said storing means connected to said carrier gas feeding means.

12. The apparatus according to claim 10, wherein said collecting means further comprise pump means for feeding a continuous flow of said aqueous solution of hydrogen peroxide through said absorption vessel, interface means provided within said vessel for absorbing said combustion products in said aqueous solution coming out from said absorption vessel.

13. The apparatus according to claim 12, wherein said absorption vessel is connected to said analytical means.

14. The apparatus according to claims 12 or 13, wherein said analysis means is selected from the group consisting of ion chromatography equipment and electrochemical analysis equipment.

15. The apparatus according to claim 9, wherein said analytical means is selected from the group consisting of a chromatograph and a mass spectrometer.

16. The apparatus according to claim 9, wherein said flash combustion reactor is a vertical reactor and is provided with supporting means to position said sample in that portion of said reactor having the highest temperature.

17. The apparatus according to claim 16, wherein said supporting means is selected from the group consisting of glass wool and quartz shavings.

18. The apparatus according to claim 9, wherein said sample feeding means is an automatic sampler.

19. The apparatus according to claim 12, wherein said interface means is selected from the group consisting of quartz shavings, glass wool and vessel portions projecting within said vessel.

20. The apparatus of claim 9, wherein said feeding means comprises oxygen gas feeding means for continuously feeding oxygen gas to said flash combustion reactor whereby said oxygen can act as both carrier gas and combustion gas.

21. The apparatus according to claim 16 wherein said vertical flash combustion reactor further comprises an empty space at the lower end thereof.

* * * * *

UNITED STATES PATENT AND TRADEMARK OFFICE
CERTIFICATE OF CORRECTION

PATENT NO. : 5,429,946
DATED : July 4, 1995
INVENTOR(S) : Baccanti

It is certified that error appears in the above-indentified patent and that said Letters Patent is hereby corrected as shown below:

Column 1, line 52, "characterised" should read --characterized--.
Column 4, line 48 "analysed" should read --analyzed--.
Column 5, line 30 "analysed" should read --analyzed--.
Column 5, line 48 "weigth" should read --weight--.
Column 6, line 27 after "continuous flow" insert --of--.
Column 6, line 35 "comprising" should read "comprises".

Signed and Sealed this

Thirty-first Day of October 1995

Attest:

BRUCE LEHMAN

*Attesting Officer*     Commissioner of Patents and Trademarks